(12) United States Patent
Nagai et al.

(10) Patent No.: US 8,017,807 B2
(45) Date of Patent: *Sep. 13, 2011

(54) TETRAHYDROXY COMPOUND, METHOD FOR PREPARING THE TETRAHYDROXY COMPOUND, AND PHOTORECEPTOR USING THE TETRAHYDROXY COMPOUND

(75) Inventors: Kazukiyo Nagai, Numazu (JP); Tamotsu Horiuchi, Tagata-gun (JP)

(73) Assignee: Ricoh Company Limited, Tokyo (JP)

( * ) Notice: Subject to any disclaimer, the term of this patent is extended or adjusted under 35 U.S.C. 154(b) by 1270 days.

This patent is subject to a terminal disclaimer.

(21) Appl. No.: 11/562,203

(22) Filed: Nov. 21, 2006

(65) Prior Publication Data

US 2007/0128530 A1    Jun. 7, 2007

(30) Foreign Application Priority Data

Dec. 1, 2005    (JP) .................................. 2005-348181

(51) Int. Cl.
*C07C 215/00*    (2006.01)

(52) U.S. Cl. ........................................................ 564/443

(58) Field of Classification Search .................... None
See application file for complete search history.

(56) References Cited

U.S. PATENT DOCUMENTS

| | | | |
|---|---|---|---|
| 5,976,746 A | 11/1999 | Tanaka et al. | |
| 6,027,846 A | 2/2000 | Shimada et al. | |
| 6,066,428 A | 5/2000 | Katayama et al. | |
| 6,172,176 B1 | 1/2001 | Tanaka et al. | |
| 6,187,492 B1 | 2/2001 | Ri et al. | |
| 6,194,535 B1 | 2/2001 | Katayama et al. | |
| 6,210,848 B1 | 4/2001 | Nagai et al. | |
| 6,316,577 B1 | 11/2001 | Shimada et al. | |
| 6,444,387 B2 | 9/2002 | Ri et al. | |
| 6,486,293 B1 | 11/2002 | Ri et al. | |
| 6,548,216 B2 | 4/2003 | Kawamura et al. | |
| 6,576,386 B1 | 6/2003 | Ri et al. | |
| 6,790,571 B2 | 9/2004 | Kawamura et al. | |
| 6,899,983 B2 | 5/2005 | Tamoto et al. | |
| 6,919,419 B2 | 7/2005 | Ri et al. | |
| 6,936,388 B2 | 8/2005 | Suzuki et al. | |
| 6,974,654 B2 | 12/2005 | Kawamura et al. | |
| 7,056,633 B2 | 6/2006 | Kawamura et al. | |
| 7,071,285 B2 | 7/2006 | Kawamura et al. | |
| 7,122,284 B2 | 10/2006 | Kawamura et al. | |
| 7,629,094 B2 * | 12/2009 | Nagai et al. .................. | 430/58.7 |
| 2004/0053152 A1 | 3/2004 | Nagai et al. | |
| 2004/0248024 A1 | 12/2004 | Suzuki et al. | |
| 2004/0253527 A1 | 12/2004 | Suzuki et al. | |
| 2005/0158641 A1 | 7/2005 | Yanagawa et al. | |
| 2005/0170272 A1 | 8/2005 | Suzuki et al. | |
| 2005/0221210 A1 | 10/2005 | Suzuki et al. | |
| 2005/0266328 A1 | 12/2005 | Yanagawa et al. | |
| 2006/0014093 A1 | 1/2006 | Li et al. | |
| 2006/0160003 A1 | 7/2006 | Nagai et al. | |
| 2007/0117033 A1 * | 5/2007 | Sugino et al. ................ | 430/58.7 |
| 2007/0254224 A1 * | 11/2007 | Sugino ....................... | 430/58.35 |
| 2008/0138728 A1 * | 6/2008 | Sugino et al. .............. | 430/58.75 |

FOREIGN PATENT DOCUMENTS

| | | | |
|---|---|---|---|
| JP | 06120541 | * | 4/1994 |
| JP | 2001-235889 | | 8/2001 |
| JP | 2002-6517 | | 1/2002 |
| JP | 2003-76043 | | 3/2003 |

OTHER PUBLICATIONS

JP06120541 machine tranlsation, 1994, p. 1-23.*
U.S. Appl. No. 12/000,239, filed Dec. 11, 2007, Fujiwara, et al.

* cited by examiner

*Primary Examiner* — Daniel Sullivan
*Assistant Examiner* — Clinton Brooks
(74) *Attorney, Agent, or Firm* — Oblon, Spivak, McClelland, Maier & Neustadt, L.L.P.

(57) ABSTRACT

A new tetrahydroxy compound having a specific structure including two 2,3-dihydroxypropyloxy groups is provided. The compound has good charge transport property. In addition, a charge transport layer including the tetrahydroxy compound or a reaction product of the tetrahydroxy compound is provided. Further, a charge transport layer coating liquid is provided which includes the tetrahydroxy compound, and an alcohol. Furthermore an electrophotographic photoreceptor is provided which includes an electroconductive substrate, a charge generation layer, a charge transport layer and an outermost layer including the tetrahydroxy compound or a reaction product of the tetrahydroxy compound.

15 Claims, 2 Drawing Sheets

FIG. 3

TETRAHYDROXY COMPOUND, METHOD FOR PREPARING THE TETRAHYDROXY COMPOUND, AND PHOTORECEPTOR USING THE TETRAHYDROXY COMPOUND

BACKGROUND OF THE INVENTION

1. Field of the Invention

The present invention relates to a tetrahydroxy compound. In addition, the present invention also relates to a charge transport material for use in organic semiconductor devices using a charge transport material such as organic photoreceptors, organic light emitting devices, organic thin film transistors, and organic solar cells. In addition, the present invention also relates to a method for preparing the tetrahydroxy compound.

2. Discussion of the Background

Inorganic semiconductor devices are typically prepared by a vacuum film forming method. In contrast, organic semiconductor devices can be prepared by a coating method. Therefore, organic semiconductor devices have the following advantages over inorganic semiconductor devices
(1) devices having a large area can be easily prepared;
(2) the devices have relatively low manufacturing costs; and
(3) the devices have good on-demand property.

Therefore, organic semiconductor devices have been actively investigated.

On the other hand, the structure of semiconductor devices have been complicated more and more and recent semiconductor devices typically have a plurality of layers to improve the functions and performances thereof. For example, organic electrophotographic photoreceptors typically have a three layer structure such that an undercoat layer, a charge generation layer, and a charge transport layer are overlaid on an electroconductive substrate (such as aluminum drums). In addition, a photoreceptor in which a protective layer is further formed on a charge transport layer as an outermost layer so that the photoreceptor has a high performance, is disclosed in published unexamined Japanese patent application No. (hereinafter referred to as JP-A) 2001-235889.

Organic light emitting devices typically have a layered structure such that plural layers such as a hole injection layer, a hole transfer layer, a light emitting layer and an electron transport layer are overlaid. Techniques such that the above-mentioned layers are formed by a coating method using an inkjet method have been proposed. In this case, it is necessary for a coating layer not to dissolve the layer on which the coating liquid is coated, i.e., it is necessary for the coating liquid not to include a solvent dissolving the layer on which the coating liquid is coated.

Thus, when a device in which an organic layer is formed on another organic layer by a coating method, the materials included in the coating liquids or the upper and lower organic layers preferably have different solvent-solubilities to prepare a device in which the upper and lower layers have clear interface.

On the other hand, a variety of charge transport materials have been proposed. Such charge transport materials typically have a formula including a benzene ring. Therefore, the variety of charge transport materials have similar solvent solubilities, and are soluble in organic solvents such as toluene, ethyl acetate and tetrahydrofuran. Almost all of such charge transport materials are hardly soluble in lower alcohol solvents such as methanol and ethanol. Therefore, if a charge transport layer coating liquid mainly including such an alcohol solvent is coated on such charge transport materials, a layered charge transport layer having a clear interface therein can be prepared. However, charge transport materials which can be well dissolved in a lower alcohol solvent have hardly be found.

JP-A2000-23589 mentioned above proposes a photoreceptor in which an alcohol soluble charge transport material is used as one component of the outermost layer thereof. It is described therein that the alcohol soluble charge transport material is compounds having a benzadine structure or a triphenylamine structure into which a carboxyl group or a hydroxy group is incorporated. In addition, it is described therein that N,N'-diphenyl-N,N'-bis(3-hydroxyphenyl)-[1,1'-biphenyl]-4,4'-diamine and another compound are used as an alcohol soluble charge transport material. However, as a result of the present inventors' study, it is found that the solubility of the compounds to methanol is insufficient. This is because the molecular weight of the compounds per one hydroxyl group is still high and therefore the compounds have low polarity.

Therefore, it is considered to be preferable that three or four hydroxyl groups are incorporated into such a compound. However, it is difficult to incorporate three or four hydroxyl groups into such a compound because the manufacturing costs of the compound seriously increase and in addition the charge transport property thereof deteriorates. Namely, a charge transport material having a good combination of charge transport property and alcohol solvent solubility has not yet been developed.

JP-A2002-6517 discloses an organic photoreceptor having a protective layer serving as an outermost layer in which an alcohol soluble charge transport material such as charge transport materials modified by a hydroxyalkyl group or a hydroxyalkoxyl group is included as one component. Specific examples of the alcohol soluble charge transport material are N,N-bis(4-hydroxyethylphenyl)-4-ethyl-3-methylaniline and three other compounds, each of which includes a 2-hydroxyethyl group as a substituent. In order to synthesis such compounds, ethylene oxide is typically used. Since ethylene oxide is a dangerous compound, it is not easy to synthesize the compounds.

JP-A2003-76043 discloses an organic photoreceptor having a protective layer serving as an outermost layer in which an alcohol soluble charge transport material such as compounds having one or two polyalkylene oxide groups as the end hydroxyl group is included as one component. Specific examples of the alcohol soluble charge transport material are 1,1-bis(4-hydroxyphenyl)-1-[4-(paraditolylamino)phenyl]ethane and five other compounds. However, as a result of the present inventors' study, it is found that the solubility of the compounds to methanol is insufficient. This is because the molecular weight of the compounds per one hydroxyl group is still high.

Because of these reasons, a need exists for an alcohol soluble charge transport material having a good charge transport property, a good solubility to lower alcohols such that the resultant alcohol solution has a solid content not lower than 20% by weight, and low manufacturing costs.

SUMMARY OF THE INVENTION

As one aspect of the present invention, a tetrahydroxy compound is provided which has the following formula (1):

(1)

wherein each of $Ar^1$ and $Ar^2$ resents a substituted or unsubstituted arylene group; X represents a divalent group having one of the following formula (2) to (4):

(2)

wherein $Ar^3$ represents a substituted or unsubstituted arylene group, each of $Ar^4$ and $Ar^5$ represents a substituted or unsubstituted aryl group, (3)

wherein $Ar^6$ represents a substituted or unsubstituted arylene group or a substituted or unsubstituted aryl group; and each of $Ar^7$ and $Ar^8$ represents a substituted or unsubstituted aryl group; and n is 0, 1 or 2, and (4)

wherein $R^1$ represents a hydrogen atom or a substituted or unsubstituted alkyl group; $Ar^9$ represents a substituted or unsubstituted arylene group; and each $Ar^{10}$ and $Ar^{11}$ represents a substituted or unsubstituted aryl group.

Among the tetrahydroxy compounds, a compound having the following formula (5) is preferable.

(5)

wherein each of $Ar^{12}$ and $Ar^{13}$ represents a substituted or unsubstituted aryl group.

As another aspect of the present invention, a coating liquid is provided which includes the above-mentioned tetrahydroxy compound, and an alcohol.

As yet another aspect of the present invention, a charge transport layer is provided which includes the above-mentioned tetrahydroxy compound or a reaction product of the tetrahydroxy compound.

As a further aspect of the present invention, a photoreceptor is provided which includes an electroconductive substrate, a charge generation layer located overlying the electroconductive substrate and including a charge generation material, a charge transport layer located overlying the charge generation layer and including a charge transport material, and an outermost layer located on the charge transport layer and including the above-mentioned tetrahydroxy compound or a reaction product of the tetrahydroxy compound.

As a still further aspect of the present invention, a method for preparing the tetrahydroxy compound is provided which includes subjecting a mixture of a diol compound and a glycidyl ester of a carboxylic acid to a ring-opening addition reaction to form a diester of the dicarboxylic acid having hydroxyl groups; and subjecting the diester of the dicarboxylic acid having hydroxyl groups to hydrolysis, or reacting epichlorohydrin with a diol compound to prepare an epoxy compound; and then subjecting the epoxy compound to a ring-opening reaction.

These and other objects, features and advantages of the present invention will become apparent upon consideration of the following description of the preferred embodiments of the present invention taken in conjunction with the accompanying drawings.

DETAILED DESCRIPTION OF THE INVENTION

In formulae (1) to (5) each of $Ar^1$, $Ar^2$, $Ar^3$ and $Ar^9$ represents a substitution or unsubstituted arylene group. In addition, in formula (3) where n is 1 or 2, $Ar^6$ also represents a substituted or unsubstituted arylene group. Specific examples of the unsubstituted arylene group include divalent groups of the aromatic hydrocarbons mentioned below.

Specific examples of the aromatic hydrocarbons from which the arylene group is derived include benzene, naphthalene, biphenyl, stilbene, and distyrylbenzene.

Specific examples of the substituents for the arylene group include halogen atoms, alkyl groups which have 1 to 6 carbon atoms and which optionally have a substituent, and alkoxyl groups which optionally have a substituent. Specific examples of the halogen atoms include fluorine, chlorine, bromine and iodine atoms. Specific examples of the alkyl groups having 1 to 6 carbon atoms include methyl, ethyl, n-propyl, iso-propyl, t-butyl, s-butyl, n-butyl, iso-butyl, n-pentyl, n-hexyl, and cyclohexyl groups, but are not limited thereto. These alkyl groups can be substituted with a halogen atom and/or a phenyl group. Suitable alkoxyl groups for use in formulae (1) to (5) include alkoxyl groups of alkyl groups having 1 to 6 carbon atoms optionally having a substituent. Specific examples of the alkoxyl groups include methoxy, ethoxy, n-propoxy, iso-propoxy, t-butoxy, n-butoxy, and benzyloxy groups, but are not limited thereto.

Among these arylene groups, phenylene groups are preferable for $Ar^1$ and $Ar^2$ and paraphenylene groups and meth- aphenylene groups are more preferable therefor. Further, among the above-mentioned substituents of the groups, alkyl ground having 1 to 6 carbon atom and alkoxyl groups are preferable, and methyl and methoxy groups are more preferable.

In formulae (1) to (5) each of $Ar^4$, $Ar^5$, $Ar^7$, $Ar^8$ and $Ar^{10}$ represents a substituted or unsubstituted aryl group. In addition, in formula (3) where n is 0, $Ar^6$ represents a substituted or unsubstituted aryl group. Specific examples of the unsubstituted aryl group include monovalent groups of the aromatic hydrocarbons mentioned below.

Specific examples of the aromatic hydrocarbons from which the aryl group is derived include benzene, naphthalene, fluorine, triphenylene, phenanthrene, anthracene, pyrene, 1,2,3,4-tetrahydronaphthalene, biphenyl, terphenyl, and stilbene.

Specific examples of the substituents for the aryl groups include halogen atoms, alkyl groups which have 1 to 6 carbon atoms and which optionally have a substituent, and alkoxyl groups which optionally have a substituent. Specific examples of the halogen atoms include fluorine, chlorine, bromine and iodine atoms. Specific examples of the alkyl groups having 1 to 6 carbon atoms include methyl, ethyl, n-propyl, iso-propyl, t-butyl, s-butyl, n-butyl, iso-butyl, n-pentyl, n-hexyl, and cyclohexyl groups, but are not limited thereto. These alkyl groups can be substituted with a halogen atom and/or a phenyl group. Suitable alkoxyl groups for use in formulae (1) to (5) include alkoxyl groups of alkyl groups having 1 to 6 carbon atoms optionally having a substituent. Specific examples of the alkoxyl groups include methoxy, ethoxy, n-propoxy, iso-propoxy, t-butoxy, n-butoxy, and benzyloxy groups, but are not limited thereto.

Specific examples of the tetrahydroxy compounds having formula (1) include the following compounds and the compounds mentioned below in Examples 1 and 2, but are not limited hereto.

-continued

Next, the method for manufacturing the tetrahydroxy compounds will be explained.

As described in the below-mentioned reaction formula, the tetrahydroxy compounds of the present invention can be prepared at a high yield by subjecting a mixture of a diol compound and a glycidyl ester of a carboxylic acid e.g., glycidyl methacrylate) to a ring-opening addition reaction to form a diester of a dicarboxylic acid having hydroxyl groups, which is an intermediate; and than subjected to the intermediate to hydrolysis.

Glycidyl methacrylate is one of preferable glycidyl esters of carboxylic acids, and can be obtained as an industrial reagent.

The ring-opening addition reaction is typical performed by dissolving a diol compound and a glycidyl ester of a carboxylic acid in a proper solvent and heating the mixture while agitating the mixture. In this case, a small amount of catalyst such as tertiary amines and quaternary ammonium salts can be used to effectively perform the reaction. Suitable solvents for use as the solvent include aromatic hydrocarbons such as toluene, esters such as ethyl acetate, and ethers such as tetrahydrofuran.

The heating is typically performed at a temperature of room temperature to 150° C., and preferably from 60° C. to 120° C. When the reaction temperature is too low, it takes a long time until the reaction is completed. In contrast, when the reaction temperature is too high, undesired side reactions are caused.

Specific examples the tertiary amine compounds for use as the catalyst in the ring-opening addition reaction include triethylamine, and benzyldiethylamine. Specific examples of the quaternary ammonium compounds for use as the catalyst in the ring-opening addition reaction include benzylethylammonium chloride and tetraethylammonium chloride. The added amount of the catalyst is generally from 0.01 to 5% by weight, and preferably from 1 to 2% by weight. The reaction time is generally from few hours to tens of hours. When the reaction is performed under preferable conditions (for example, under proper conditions with respect to the reaction on temperature and added amount of catalyst) the reaction time is typically from 5 to 10 hours.

In order to rapidly subject the thus prepared intermediate (i.e., a diester of a dicarboxylic acid having a hydroxyl group) to hydrolysis, an inorganic salt such as sodium hydroxide is added to the intermediate while heating and agitating the mixture. In this case, the reaction temperature is generally from room temperature to 100° C., and preferably from 60° C. to 95° C. The hydrolysis reaction is typically completed in a time of about few hours.

In addition, the tetrahydroxy compounds can also be prepared by reacting epichlorohydrin with a diol compound to prepare an epoxy compound and then subjecting the epoxy compound to a ring-opening reaction as illustrated in the following reaction formula.

Next, the photoreceptor of the present invention will be explained.

Figure 3:
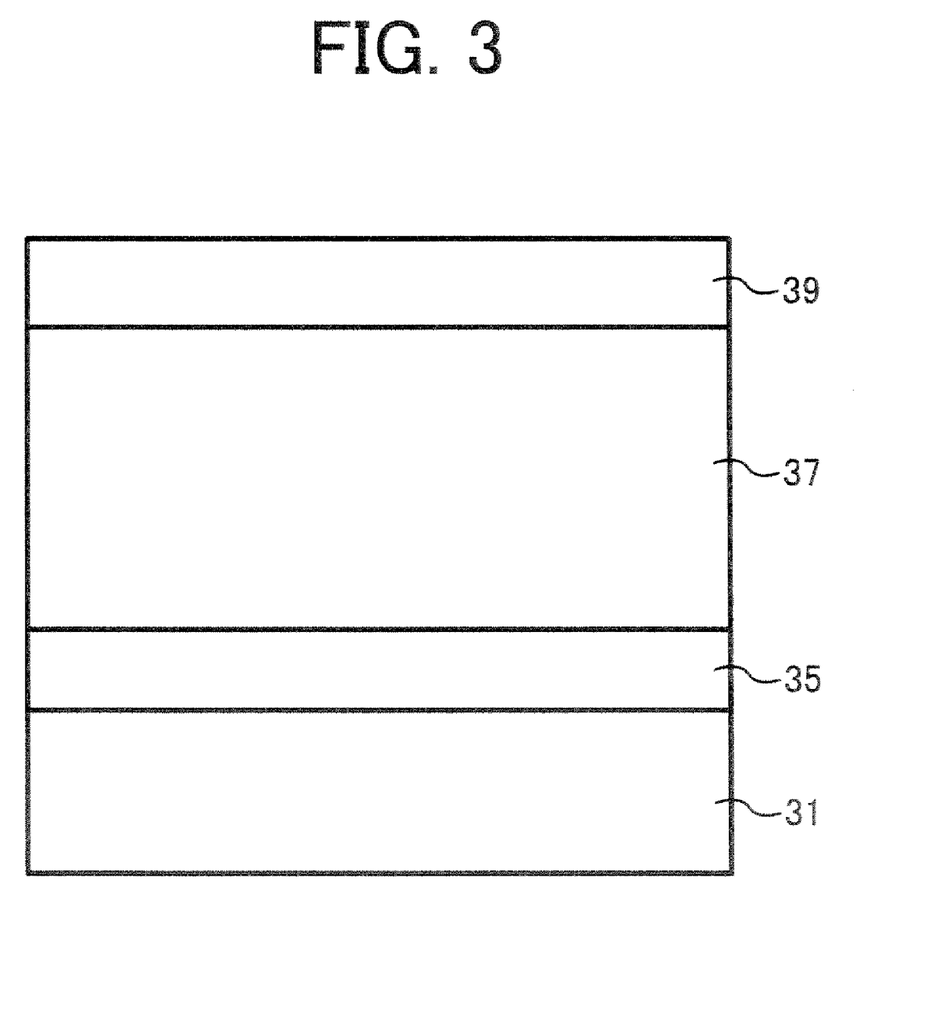
FIG. 3 is a schematic view illustrating the cross section of an example of the photoreceptor of the present invention.

The photoreceptor of the present invention preferably has a structure illustrated in FIG. 3.

In FIG. 3, a charge generation layer 35 including a charge generation material as a main component and a charge transport layer 37 including a charge transport material as a main component are overlaid on an electroconductive substrate 31 in this order. In addition, an outermost layer 39 (or a second charge transport layer) is formed on the CTL 37. The outermost layer 39 includes the tetrahydroxyl compound of the present invention or a reaction product of the tetrahydroxyl compound.

Then the electroconductive substrate 31, and the layers will be explained.

Suitable materials for use as the electroconductive substrate 31 include materials having a volume resistivity not greater than $10^{10}$ Ω·cm. Specific examples of such materials include plastic cylinders, plastic films or paper sheets, on the surface of which a metal such as aluminum, nickel, chromium, nichrome, copper, gold, silver, platinum and like, or a metal oxide such as tin oxides, indium oxides and the like, is formed by deposition or sputtering. In addition, a plate of a metal such as aluminum, aluminum alloys, nickel and stainless steel can be used. A metal cylinder can also be used as the substrate 1, which is prepared by tubing a metal such a aluminum, aluminum alloys, nickel and stainless steel by a method such as impact ironing or direct ironing, and then treating the surface of the tube by cutting, super finishing, polishing and the like treatments. Further, endless belts of a metal such as nickel, stainless steel and the like can also be used as the substrate 31.

Furthermore, substrates, in which a coating liquid including a binder resin and an electroconductive powder is coated on the supports mentioned above, can be used as the substrate 31. Specific examples of such an electroconductive powder include carbon black, acetylene black, powders of metals such as aluminum, nickel, iron, nichrome, copper, zinc, silver and the like, and metal oxides such as electroconductive tin oxides, ITO and the like. Specific examples of the binder resin include known thermoplastic resins, thermosetting resins and photo-crosslinking resins, such as polystyrene, styrene-acrylonitrile copoloymers, styrene-butadiene copolymers, styrene-maleic anhydride copolymers, polyesters, polyvinyl chloride, vinyl chloride-vinyl acetate copolymers, polyvinyl acetate, polyvinylidene chloride, polyarylates, phenoxy resins, polycarbonates, cellulose acetate resins, ethyl cellulose resins, polyvinyl butyral resins, polyvinyl formal resins, polyvinyl toluene, poly-N-vinyl carbazole, acrylic resins, silicone resins, epoxy resins, melamine resins, urethane resins, phenolic resins, alkyd resins and the like resins.

Such an electroconductive layer can be formed by coating a coating liquid in which an electroconductive powder and a binder resin are dispersed or dissolved in a proper solvent such as tetrahydrofuran, dichloromethane, methyl ethyl ketone, toluene and the like solvent, and then drying the coated liquid.

In addition, substrates, in which an electroconductive resin film is formed on a surface of a cylindrical substrate using a heat-shrinkable resin tube which is made of a combination of a resin such as polyvinyl chloride, polypropylene, polyesters, polyvinylidene chloride, polyethylene, chlorinated rubber and fluorine-containing resins (such as TEFLON), with an electroconductive material, can also be used as the substrate 31.

The charge generation layer 35 (hereinafter referred to as the CGL 35) includes a charge generation material as a main component, and optionally a binder resin is also used. In the CGL 35, known inorganic and organic charge generation materials can be used.

Specific examples of the inorganic charge generation materials include crystal selenium, amorphous selenium, selenium-tellurium compounds, selenium-tellurium-halogen compounds, selenium-arsenic compounds, amorphous silicon, etc. With respect to amorphous silicon, compounds in which the dangling bond is terminated with a hydrogen atom or a halogen atom or in which a boron atom or a phosphorus atom is doped can be preferably used.

Suitable organic charge generation materials include known organic charge generation material. Specific examples of the organic charge generation materials include phthalocyanine pigments such as metal phthalocyanine and metal-free phthalocyanine, azulenium pigments, squaric acid methine pigments, azo pigments having a carbazole skeleton, azo pigments having a triphenylamine skeleton, azo pigments having a diphenylamine skeleton, azo pigments having a dibenzothiophene skeleton, azo pigments having a fluorenone skeleton, azo pigments having an oxadiazole skeleton, azo pigments having a bisstilbene skeleton, azo pigments having a distyryloxadiazole skeleton, azo pigments having a distyrylcarbazole skeleton, perylene pigments, anthraquinone pigments, polycyclic quinone pigments, quinoneimine pigments, diphenyl methane pigments, triphenyl methane pigments, benzoquinone pigments, naphthoquinone pigments, cyanine pigments, azomethine pigments, indigoid pigments, bisbenzimidazole and the like materials. These charge transport materials can be used alone or in combination.

Specific examples of the binder resin, which is optionally used in the charge generation layer 35, include polyamide resins, poly urethane resins, epoxy resins, polyketone resins, polycarbonate resins, silicone resins, acrylic resins, polyvinyl butyral resins, polyvinyl formal resins, polyvinyl ketone resins, polystyrene resins, poly-N-vinylcarbazole resins, polyacrylamide resins, and the like.

The addition quantity of the binder resin is from 0 to 500 parts by weight, and preferably from 10 to 300 parts by weight, per 100 parts by weight of the charge generation material included in the charge generation layer 35.

Suitable methods for forming the charge generation layer 35 include thin film forming methods in a vacuum, and casting methods using a coating liquid.

Specific examples of such thin film forming methods in a vacuum include vacuum evaporation methods, glow discharge decomposition methods, ion plating methods, sputtering methods, reaction sputtering methods, CVD (chemical vapor deposition) methods, and the like methods. A layer of the above-mentioned inorganic and organic materials can be formed by one of these methods.

The casting methods useful for forming the charge generation layer 35 include, for example, the following steps:
(1) preparing a coating liquid by mixing one or more inorganic or organic charge generation materials mentioned above with a solvent such as tetrahydrofuran, cyclohexanone, dioxane, dichloroethane, butanone and the like, and if necessary, together with a binder resin and an additives, and then dispersing the materials with a ball mill, an attritor, a sand mill or the like;
(2) coating on a substrate the coating liquid, which is diluted if necessary, by a dip coating method, a spray coating method, a bead coating method, a nozzle coating method, a spinner coating method, a ring coating method or the like method; and
(3) drying the coated liquid to form a charge generation layer.

The thickness of the charge generation layer 35 is preferably from about 0.01 to about 5 µm, and more preferably from about 0.1 to about 2 µm.

The charge transport layer 37 (hereinafter referred to as a CTL 37) can be formed, for example, by the following method:
(1) a charge transport material and a binder resin are dispersed or dissolved in a proper solvent to prepare a CTL coating liquid; and
2) the coating liquid is coated on the CGL 35 and dried no form a charge transport layer.

The CTL 37 may include additives such as plasticizers, leveling agents, antioxidants and the like if desired.

Charge transport materials are classified into positive-hole transport materials and electron transport materials.

Specific examples of the electron transport materials include electron accepting materials such as chloranil, bromanil, tetracyanoethylene, tetracyanoquinodimethane, 2,4,7-trinitro-9-fluorenon, 2,4,5,7-tetranitro-9-fluorenon, 2,4,5,7-tetanitroxanthone, 2,4,8-trinitrothioxanthone, 2,6,8-trinitro-4H-indeno[1,2-b]thiophene-4-one, 1,3,7-trinitrodibenzothiphene-5,5-dioxide, benzoquinone derivatives and the like.

Specific examples of the positive-hole transport materials include known materials such as poly-N-carbazole and its derivatives, poly-γ-carbazolylethylglutamate and its derivatives, pyrene-formaldehyde condensation products and their derivatives, polyvinyl pyrene, polyvinyl phenanthrene, polysilane, oxazole derivatives, oxadiazole derivatives, imidazole a derivatives, monoarylamines, diarylamines, triarylamines, stilbene derivatives, α-phenyl stilbene derivatives, benzidine derivatives, diarylmethane derivatives, triarylmethane derivatives, 9-styrylanthracene derivatives, pyrazoline derivatives, divinyl benzene derivatives, hydrazone derivatives, indene derivatives, butadiene derivatives, pyrene derivatives, bisstilbene derivatives, enamine derivatives, and the like.

These charge transport materials can be used alone or in combination.

Specific examples of the binder resin for use in the CTL 37 include known thermoplastic resins, thermosetting-resins and photo-crosslinking resin, such as polystyrene, styrene-acrylonitrile copolymers, styrene-butadiene copolymers, styrene-maleic anhydride copolymers, polyesters, polyvinyl chloride, vinyl chloride-vinyl acetate copolymers, polyvinyl acetate, polyvinylidene chloride, polyarylates, phenoxy resins, polycarbonates, cellulose acetate resins, ethyl cellulose resins, polyvinyl butyral resins, polyvinyl formal resins, polyvinyl toluene, poly-N-vinyl carbazole, acrylic resins, silicone resins, epoxy resins, melamine resins, urethane resins, phenolic resins, alkyd resins and the like.

The content of the charge transport material in the CTL 37 is preferably from 20 to 300 parts by weight, and more preferably from 40 to 105 parts by weight, per 100 part by weight of the binder resin included in the CTL 37. The thickness of the CTL 37 is preferably from 5 to 100 µm.

Suitable solvents for use in the coating liquid include tetrahydrofuran, dioxane, toluene, dichloromethane, monochlorobenzene, dichloroethane, cyclohexanone, methyl ethyl ketone, acetone and the like solvents.

The CTL 37 preferably includes a charge transport polymer, which has both a binder resin function and a charge transport function. The CTL 37 constituted of a charge transport polymer has good abrasion resistance.

Suitable charge transport polymers include known charge transport polymers. Among these polymers, polycarbonate resins having a triarylamine structure in their main chain and/or side chain are preferably used.

The outermost layer 39 includes the tetrahydroxy compound mentioned above or a reaction product of the tetrahydroxy compound. When the tetrahydroxy compound mentioned above is used for the outermost layer, the compound is preferably used in combination with an alcohol soluble film forming resin.

Specific examples of the alcohol-soluble resins include polyamide resins (including nylons and modified nylons), polyvinyl butyral resins, cellulose resins, etc.

When a reaction product of the tetrahydroxy compound is used for the outermost layer, an alcohol-soluble monomer reactive with the tetrahydroxy compound is preferably used.

Specific examples of the alcohol-soluble monomer include silane compounds having one of the following formulae (A) and (B):

(A)

(B)

In formula (A), R represents an organic group having a carbon atom directly connected to the silicon atom in the center of formula (A); X represents a group having hydrolysis ability; and n is 0 or an integer of from 1 to 3.

Specific examples of the organic group having a carbon atom directly connected to the silicon atom include alkyl groups such as methyl, ethyl, and propyl groups; aryl groups such as phenyl, tolyl, naphthyl, and biphenyl groups; halogenated alkyl groups such as γ-chloropropyl, 1,1,1-trifluoropropyl, nonafluorohexyl, and perfluorooctylethyl groups; amono-substituted alkyl groups; cyano-substituted alkyl groups; epoxy-substituted alkyl groups; cyclohexeneoxide-substituted alkyl groups; tricyclodeceneoxide-substituted alkyl groups; cyclopenteneoxide-substituted alkyl groups; amino-substituted phenyl groups; etc.

Specific examples of the groups having hydrolysis ability include alkoxyl groups such as methoxy, ethoxy, propoxy, and butoxy groups; halogen atoms; acyloxy groups; etc. Among these groups, alkoxyl groups having not greater than 6 carbon atoms are preferable.

The compounds having formula (A) are used alone or in combination.

In formula (B), R represents an organic group having a carbon atom directly connected to the silicon atom in the center of formula (B); n is 0 or an integer of from 1 to 3; and Y represents a hydroxy group or a group having hydrolysis ability, wherein when n is 3, Y represents a hydroxyl group, and when n is less than 3, Y represents a combination of at least one hydroxyl group and one or more groups selected from the groups consisting of hydrogen atom and hydrolysis groups when n is less than 3.

Specific examples of the organic group having a carbon atom directly connected to the silicon atom in the center of formula (B) are the groups mentioned above for use in formula (A). Specific examples of the groups having hydrolysis ability are groups mentioned above for use in formula (A).

Specific examples of the silane compounds include trimethylmethoxysilane, dimethyldimethoxysilane, methyltrimethoxysilane, trimethylethoxysilane, dimethyldiethoxysilane, methyltriethoxysilane, propyltrimethoxysilane, n-butyltrimethoxysilane, phenyltrimethoxysilane, phenyltriethoxysilane, 3-glycidoxypropyltrimethoxysilane, 3-glycidoxypropylmethyldimethoxysilane, 2-(3,4-epoxycyclohexyl)ethyltrimethoxysilane, 2-(3,4-epoxycyclohexyl)ethyltriethoxysilane, 5,6-epoxyhexyltriethoxysilane, 4-aminobutyltriethoxysilane, N-(2-aminoethyl)-3-aminoisobutylmethyldimethoxysilane, (aminoethylaminomethyl)phenethyltrimethoxysilane, N-(2-aminoethyl)-3-aminopropylmethyldimethoxysilane, N-(2-aminoethyl)-3-aminopropyltrimethoxysilane, aminophenyltrimethoxysilane, 3-aminopropylmethyldiethoxysilane, 3-aminopropyltriethoxysilane, 3-aminopropyltrimethoxysilane, and hydrolysis products of these silane compounds.

It is preferable to form the outermost layer by coating a coating liquid including the tetrahydroxyl compound and an alcohol solvent on a charge transport layer insoluble in the alcohol solvent so as not to dissolve the charge transport layer.

The structure of the photoreceptor of the present invention is not limited to the structure illustrated in FIG. 3. For example, a charge blocking layer and a moiré preventing layer can be provided between the electroconductive substrate 31 and the charge generation layer.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Example 1

Preparation of N-{4-[2,2-bis(4-(2,3-dihydroxypropyloxy)phenyl)vinyl]phenyl}-N,N-bis(4-tolyl)amine At first, the following compounds were contained in a reaction vessel.

| | |
|---|---|
| N-{4-[2,2-bis(4-hydroxyphenyl)vinyl]phenyl}-N,N-bis(4-tolyl)amine | 14.51 g |
| Glycidyl methacrylate | 9.45 g |
| Toluene | 20 ml |

After the mixture was heated to 90° C. while agitated, 0.24 g of triethylamine was added thereto. After the mixture was heated to 95° C. while agitated, the mixture was agitated for 7.5 hours to perform a reaction. After the reaction product was cooled, 30 ml of a 10% aqueous solution of sodium hydroxide and 15 ml of toluene were added thereto. After the mixture was heated to 90° C. while agitated, the mixture was agitated for 3 hours to perform a reaction.

After the reaction product was cooled, 60 ml of water, 100 ml of a 0.5N aqueous solution of hydrochloric acid were added thereto and then the reaction product was extracted with ethyl acetate. After the thus obtained organic phase was washed with a dilute hydrochloric acid, followed by washing with a saturated solution of sodium chloride, anhydrous magnesium sulfate was added thereto to remove water. After the product was filtered and condensed, a mixture solvent of ethyl acetate and tetrahydrofuran was added thereto. The solution was subjected to a column refinement treatment using silica gel. As a result, 13.29 g of a yellow amorphous material, which is the target compound, could be obtained at a yield of 70%.

Figure 1:
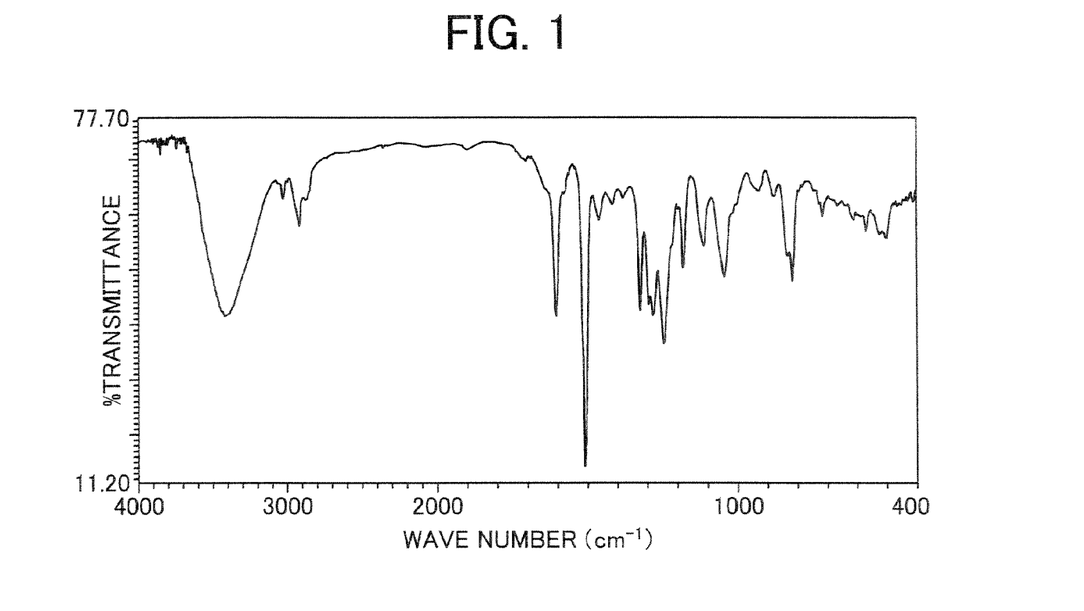
FIG. 1 illustrates the infrared absorption spectrum of the compound prepared in Example 1.

The thus prepared material had a m/z ratio of 632, which was determined by ionizing the material by an atmospheric chemical ionization method and measuring in a positive mode. The m/z ratio is identical with the sum of the molecular weight (631.77), which is calculated from the formula of N-{4-[2,2-bis(4-(2,3-dihydroxypropyloxy)phenyl)vinyl]phenyl}-N,N-bis(4-tolyl)amine, and one (i.e., a proton). The infrared absorption spectrum of the material is illustrated in FIG. 1.

As mentioned above, by subjecting a bisphenol derivative and a glycidyl ester of methacrylic acid to a ring-opening reaction, followed by hydrolysis, a material having two 2,3- dihydroxypropyloxy groups can be easily prepared. Thus, a charge transport material having four hydroxyl groups can be easily prepared.

Evaluation of the Material

1. Solubility to Alcohol

The above-prepared charge transport material (i.e., N-{4-[2,2-bis(4-(2,3-dihydroxypropyloxy)phenyl)vinyl]phenyl}-N,N-bis(4-tolyl)amine, hereinafter referred to as the compound of Example 1) and comparative hydroxy materials having the following formula (6), (7), (8) or (9) were evaluated by the below-mentioned method.

(6)

(7)

(8)

(9)

Each of the compound of Example 1 and comparative compounds (6) to (9) was dissolved in methanol to prepare methanol solutions thereof having a solid content of 5%, 10%, 20%, 30%, 40%, 50% or 60% by weight. After the solutions were allowed to settle for one hour at room temperature, the solutions were visually observed to determine the solubility of the compounds to methanol. The solubility to methanol was graded as follows:

○: The compound is perfectly dissolved in methanol, and the resultant liquid contains no solid material.

X: The compound is imperfectly dissolved in methanol and the resultant liquid contains a solid material or is opaque (i.e., is not transparent).

The results are shown in Table 1.

In addition, each of the compound of Example 1 and comparative compounds (6) to (9) was mixed with an alcohol-soluble polyamide resin (CM8000 from Toray Industries, Inc.) in a weight ratio of 1:1 such that the solid content of the mixture is 20% by weight. Each of the mixtures was coated on an aluminum plate by a blade coating method and then dried at room temperature (23° C.) to prepare a layer with a thickness of 20 μm. The thus prepared layers were visually observed to determine the film formability of the layers. The film formability was graded as follows:

○: The resultant layer is transparent.

X: The resultant layer is opaque due to crystallization of the compounds or bad compatibility with the resin.

The results are shown in Table 2.

TABLE 1

| Compound | Solid content (% by weight) | | | | | | |
|---|---|---|---|---|---|---|---|
| | 5% | 10% | 20% | 30% | 40% | 50% | 60% |
| Compound of Ex. 1 | ○ | ○ | ○ | ○ | ○ | ○ | ○ |
| Comp. compound (6) | ○ | ○ | ○ | ○ | X | X | X |
| Comp. compound (7) | ○ | ○ | ○ | X | X | X | X |
| Comp. compound (8) | ○ | ○ | ○ | ○ | X | X | X |
| Comp. compound (9) | X | X | X | X | X | X | X |

TABLE 2

| Compound | Film formability |
|---|---|
| Compound of Ex. 1 | ○ |
| Comp. compound (6) | X |
| Comp. compound (7) | X |
| Comp. compound (8) | X |
| Comp. compound (9) | It was impossible to prepare a coating liquid. |

It is clear from Tables 1 and 2 that the compound of Example 1 has a good solubility to methanol and a good film formability when mixed with an alcohol-soluble resin.

Applied Example 1

Preparation of Undercoat Layer

The following components were mixed to prepare an undercoat layer coating liquid.

| | |
|---|---|
| Alkyd resin (BEKKOSOL 1307-60-EL from Dainippon Ink & Chemicals, Inc.) | 6 parts |
| Melamine resin (SUPER BEKKAMIN G-821-60 from Dainippon Ink & Chemicals) | 4 parts |
| Titanium oxide | 40 parts |
| Methyl ethyl ketone | 50 parts |

The thus prepared undercoat layer coating liquid was coated on an aluminum cylinder having a diameter of 30 mm, and the coated liquid was dried to form an undercoat layer having a thickness of 3.5 μm.

Preparation of Charge Generation Layer

A dispersion (i.e., a charge generation layer coating liquid) was prepared using the following components.

| | |
|---|---|
| Polyvinyl butyral (XYHL from Union Carbide Corp.) | 0.5 parts |
| Cyclohexanone | 200 parts |
| Methyl ethyl ketone | 80 parts |
| Azo pigment having the following formula | 2.4 parts |

2-[2-hydroxy-3-(2-chlorophenyl)carbamoyl-1-naphthylazo]-7-[2-hydroxy-3-(3-methylphenyl)carbamoyl-1-naphthylazo]fluorine-9-one

At first, the polyvinyl butyral resin was dissolved in a mixture of cyclohexanone and methyl ethyl ketone. Then the azo pigment was mixed with the resin solution and the mixture was subjected to a dispersion treatment. Thus, a dispersion was prepared.

This charge generation layer coating liquid was coated on the undercoat layer and the coated liquid was dried to form a charge generation layer having a thickness of 0.2 μm.

Preparation of Charge Transport Layer

The following components were mixed to prepare a charge transport layer coating liquid.

| | |
|---|---|
| Polycarbonate (PANLITE TS-2050 from Teijin Chemicals Ltd.) | 10 parts |
| CTM having the following formula | 7 parts |

[4-(2,2-diphenylvinyl)phenyl]-di-para-tolylamine

Tetrahydrofuran 80 parts

1% tetrahydrofuran solution of silicone oil 0.2 pats (silicone oil: KF-50-100CS from Shin-Etsu Chemical Co., Ltd.)

The thus prepared charge transport layer coating liquid was coated on the charge generation layer and then the coated liquid was dried. Thus a charge transport layer having a thickness of 18 μm was prepared.

Preparation of Crosslinked Charge Transport Layer Using Sol-Gel Method

The following components were mixed.

| | |
|---|---|
| Methyl trimethoxy silane (LS-530 from Shin-Etsu Chemical Co., Ltd.) | 1.5 g |
| Compound of Ex. 1 | 1.5 g |
| 1% aqueous solution of acetic acid | 0.05 g |
| Methanol | 12 g |

The mixture was agitated for one hour at room temperature to perform a reaction. Then 53.4 mg of tris(2,4-pentanedionate)aluminum (III) was added to the mixture to prepare a coating liquid including methanol as a solvent.

The coating liquid was coated on the above-prepared charge transport layer by a spray coating method and then dried to form an outermost layer with a thickness of 2 μm. The photoreceptor was heated for 1 hour at 130° C. to crosslink the outermost layer.

Thus, a photoreceptor was prepared.

The photoreceptor was set in the main body of the image forming apparatus (IMAGIO NEO) to produce images. The resultant images had good image qualities. Therefore, it is clear that the compound of Example 1 has good charge transport property.

Comparative Examples 1 to 4

The procedure for preparation of the outermost layer in Applied Example 1 was repeated except that the compound of Example 1 was replaced with each of the comparative compounds (6) to (9).

As a result, coating liquids could not be prepared using the comparative compounds (6), (7) and (9) because the compounds have poor solubility to methanol. A coating liquid could be prepared using the comparative compound (8) but the resultant coated layer was opaque due to occurrence of phase separation. Therefore, the layer could not be well crosslinked, and thereby the photoreceptor could not be used for the image forming apparatus.

Thus, it is clear from the above description that the compound of Example 1 has a good combination of solubility, film formability and non-crystallinity, and can be used at a high concentration for coating liquids including an alcohol as a solvent. Therefore, the compound can be used for various applications.

Example 2

Preparation of N,N'-diphenyl-N,N'-bis[4-(2,3-dihydroxypropyloxy)phenyl]benzidine (1) Preparation of intermediate (i.e., N,N'-diphenyl-N,N'-bis-4-methoxyphenylbenzidine)

The following components were fed into a reaction vessel equipped with a stirrer, a thermometer and a condenser.

| N,N'-diphenylbenzidine | 4.98 g |
|---|---|
| 4-bromoanisole | 6.22 g |
| Potassium t-butoxide | 4.54 g |
| Palladium acetate | 0.03 g |
| Xylene | 80 ml |

After the mixture was mixed at room temperature under a nitrogen gas flow, 0.2 ml of tri-t-butyl phosphine was added thereto. Then the mixture was heated for four hours at 120° C. to perform a reaction. After the reaction product was cooled to room temperature, the product was passed through a silica gel chromatography to remove undesired materials therefrom. After the resultant filtrate was condensed, the residue was refined using a silica gel chromatography using a mixture solvent in which n-hexane and toluene are mixed in a weight ratio of 2/3. As a result, 4.35 g of a white crystal having a melting point of from 134.5 to 135.5° C. was obtained. The yield was 53.6%.

(2) Preparation of intermediate (i.e., N,N'-diphenyl-N,N'-bis-4-hydroxyphenylbenzidine)

The following components were fed into a reaction vessel equipped with a stirrer, a thermometer and a condenser.

| N,N'-diphenyl-N,N'-bis-4-methoxyphenylbenzidine | 3.26 g |
|---|---|
| Methylene chloride | 30 ml |

After the mixture was cooled with ice, and then 13 ml of a 1M methylene chloride solution of boron tribromide was dropped thereinto. The mixture was further cooled with ice to perform a reaction. The reaction product was fed into ice water, followed by an extraction treatment using methylene chloride. After the resultant organic phase was washed with water, the organic phase is separated from the aqueous phase. After the organic phase liquid was dried using magnesium sulfate, the liquid was condensed under a reduced pressure. The residue was refined using a silica gel chromatography using a mixture solvent in which toluene and ethyl acetate are mixed in a weight ratio of 9/1. As a result, 2.87 g of a pale yellow crystal having a melting point of from 229.0 to 230.0° C. was obtained. The yield was 92.8%.

(3) Preparation of N,N'-diphenyl-N,N'-bis[4-(2,3-dihydroxypropyloxy)phenyl-]benzidine The following components were fed into a reaction vessel equipped with a stirrer, a thermometer and a condenser.

| N,N'-diphenyl-N,N'-bis-4-hydroxyphenylbenzidine | 20.8 g |
|---|---|
| Glycidyl methacrylate | 12.3 ml |
| Toluene | 50 ml |

After the mixture was heated to 90° C., 0.36 g of triethylamine was added thereto. The mixture was heated to 95° C. and subjected to a reaction for 7 hours.

Then 40 ml of a 10% aqueous solution of sodium hydroxide and 40 ml of toluene were added thereto, and the mixture was reacted for two hours at 94° C.

After the reaction was completed, the reaction product was subjected to an extraction treatment. After the organic phase liquid was neutralized and washed, the organic phase liquid was separated from the aqueous phase liquid and then condensed under a reduced pressure. After the residue was washed with hexane, the residue was refined using a silica gel chromatography using a mixture solvent in which ethyl acetate and tetrahydrofuran are mixed in a weight ratio of 1/1. As a result, 17.8 g of a colorless noncrystalline material (i.e., the target material) was obtained. The yield was 67%.

Figure 2:
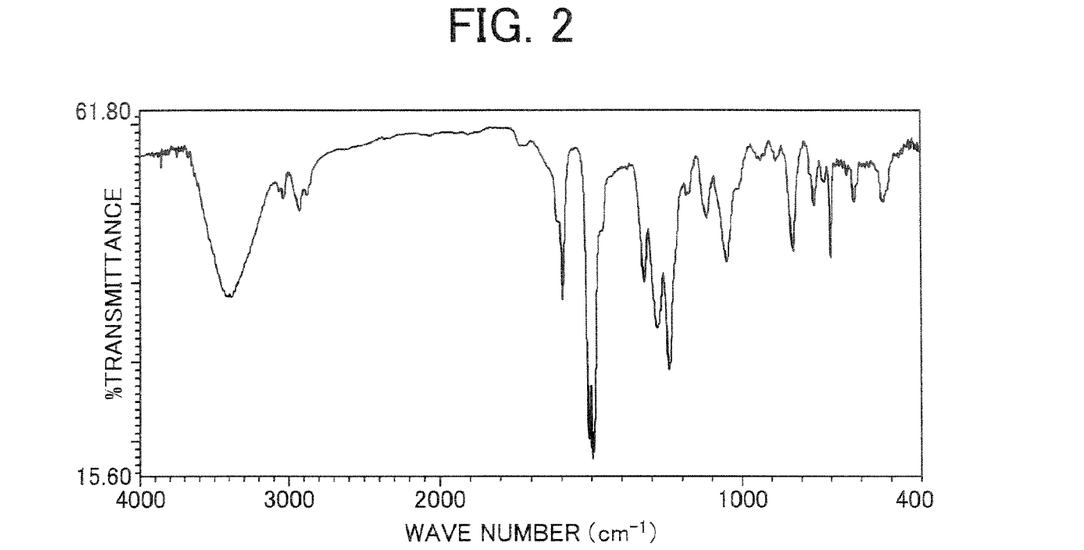
FIG. 2 illustrates the infrared absorption spectrum of the compound prepared in Example 2.

The material had a m/z ratio of 669, which was determined by ionizing the material by an atmospheric chemical ionization method and measuring in a positive mode. The m/z ratio is identical with the sum of the molecular weight (668.79), which is calculated from the formula of N,N'-diphenyl-N,N'-bis[4-(2,3-dihydroxypropyloxy)phenyl]benzidine, and one (i.e., a proton). The infrared absorption spectrum of the material is illustrated in FIG. 2.

This material has as good solubility to methanol and film formability as the compound of Example 1.

As mentioned above, the alcohol soluble charge transport material of the present invention has a charge transport structure and four electron accepting hydroxyl groups which are connected with the donor group with a short non-conjugated connection group therebetween. Therefore, the material can be dissolved in a lower alcohol at a high concentration. Thus, it becomes possible to provide an alcohol soluble charge transport material having good charge transport property.

In addition, 2,3-dihydroxypropyloxy group can be easily introduced at a high yield using derivative of a diol compound and an industrial reagent. Therefore, the charge transport material of the present invention has Low manufacturing costs. Further, since two 2,3-dihydroxypropyloxy groups are incorporated, the material has an asymmetric structure. Therefore, the material is non-crystalline, and thereby a good coating layer can be formed with hardly causing coating defects due to crystallization of the material and a phase separation problem in that the material is separated from the mixed material. Therefore, a charge transport material, which can be used for various applications because of forming a stable organic amorphous layer, can be provided.

The alcohol soluble charge transport material having formula (5) has a diarylaminostilbene structure, which has a good hole mobility. In addition, the material has a good solubility to alcohols without changing the energy level and the charge transport ability. This is because the 2,3-dihydroxypropyloxy group capable of imparting good alcohol solubility to the material is located at a position far from the hopping site (i.e., the triarylamine structure).

Thus, an alcohol soluble charge transport material having good charge transport ability can be provided.

This document claims priority and contains subject matter related to Japanese Patent Application No. 2005-348181, filed on Dec. 1, 2005, incorporated herein by reference.

Having now fully described the invention, it will be apparent to one of ordinary skill in the art that many changes and modifications can be made thereto without departing from the spirit and scope of the invention as set forth therein.

What is claimed as new and desired to be secured by Letters Patent of the United States is:

1. A tetrahydroxy compound having the following formula (1):

wherein each of $Ar^1$ and $Ar^2$ represents a substituted or unsubstituted arylene group; X represents a divalent group having one of the following formulae (2) to (4):

wherein $Ar^3$ represents a substituted or unsubstituted arylene group; each of $Ar^4$ and $Ar^5$ represents a substituted or unsubstituted aryl group, wherein $Ar^6$ represents a substituted or unsubstituted arylene group or a substituted or unsubstituted aryl group; and each of $Ar^7$ and $Ar^8$ represents a substituted or unsubstituted aryl group; and n is 0, 1 or 2, and wherein $R^1$ represents a hydrogen atom or a substituted or unsubstituted alkyl group; $Ar^9$ represents a substituted or unsubstituted arylene group; and each of $Ar^{10}$ and $Ar^{11}$ represents a substituted or unsubstituted aryl group.

2. The tetrahydroxy compound according to claim 1, wherein the tetrahydroxy compound has the following formula (5):

wherein each of $Ar^{12}$ and $Ar^{13}$ represents a substituted or unsubstituted aryl group.

3. A charge transport layer comprising:
the tetrahydroxy compound according to claim 1 or a reaction product of the tetrahydroxy compound.

4. A coating liquid comprising:
the tetrahydroxy compound according to claim 1; and
an alcohol.

5. The coating liquid according to claim 4, further comprising a member selected from the group consisting of alcohol-soluble monomers reactive with the tetrahydroxy compound and alcohol-soluble film forming resins.

6. An electrophotographic photoreceptor comprising:
an electroconductive substrate; and
a charge generation layer located overlying the electroconductive substrate and comprising a charge generation material;
a charge transport layer located overlying the charge generation layer and comprising a charge transport material; and
an outermost layer located on the charge transport layer and comprising the tetrahydroxy compound according to claim 1 or a reaction product of the tetrahydroxy compound.

7. The electrophotographic photoreceptor according to claim 6, wherein the tetrahydroxy compound has the following formula (5):

wherein each of $Ar^{12}$ and $Ar^{13}$ represents a substituted or unsubstituted aryl group.

8. The electrophotographic photoreceptor according to claim 6, the outermost layer including the tetrahydroxy compound according to claim 1, wherein the outermost layer further comprises a film forming resin.

9. The electrophotographic photoreceptor according to claim 8, wherein the film forming resin is soluble in an alcohol.

10. The electrophotographic photoreceptor according to claim 9, wherein the charge transport layer is insoluble in the alcohol.

11. The electrophotographic photoreceptor according to claim 6, the outermost layer including a reaction product of the tetrahydroxy compound, wherein the reaction product is crosslinked.

12. The electrophotographic photoreceptor according to claim 11, the outermost layer including a reaction product of the tetrahydroxy compound, wherein the outermost layer is prepared by a method comprising:
preparing a coating liquid including the tetrahydroxy compound, an alcohol-soluble monomer reactive with the tetrahydroxy compound and an alcohol;
coating the coating liquid; and then heating the coated layer to react the tetrahydroxy compound with the alcohol-soluble monomer.

13. The electrophotographic photoreceptor according to claim 12, wherein the charge transport layer is insoluble in the alcohol.

14. A method for preparing the tetrahydroxy compound according to claim 1, comprising:
subjecting a mixture of a diol compound and a glycidyl ester of a carboxylic acid to a ring-opening addition reaction to from a diester of the dicarboxylic acid having hydroxyl groups; and subjecting the diester of the dicarboxylic acid having hydroxyl groups to hydrolysis.

15. A method for preparing the tetrahydroxy compound according to claim 1, comprising:
reacting epichlorohydrin with a diol compounded to prepare an epoxy compound; and
then subjecting the epoxy compound to a ring-opening reaction.

* * * * *